United States Patent [19]

Prencipe et al.

[11] Patent Number: 5,385,729
[45] Date of Patent: Jan. 31, 1995

[54] VISCOELASTIC PERSONAL CARE COMPOSITION

[75] Inventors: Michael Prencipe, East Windsor; Angelo Zaccagnino, South River, both of N.J.

[73] Assignee: Colgate Palmolive Company, Piscataway, N.J.

[21] Appl. No.: 933,851

[22] Filed: Aug. 24, 1992

Related U.S. Application Data

[63] Continuation-in-part of Ser. No. 738,766, Aug. 1, 1991, Pat. No. 5,202,112.

[51] Int. Cl.⁶ .............. A61K 7/06; A61K 7/48
[52] U.S. Cl. .............. 424/70.11; 514/772.1; 514/772.6; 514/772.5
[58] Field of Search .............. 424/49, 52, 71, 70, 424/78.02, 78.05; 526/271; 514/846

[56] References Cited

U.S. PATENT DOCUMENTS

| | | | |
|---|---|---|---|
| 4,310,516 | 6/1982 | Chang et al. | 514/786 |
| 4,534,981 | 8/1985 | Zabotto et al. | 514/786 |
| 4,962,185 | 10/1990 | Tazi et al. | 526/271 |
| 4,992,517 | 2/1991 | Tazi et al. | 526/271 |
| 5,034,488 | 9/1991 | Tazi et al. | 526/271 |
| 5,202,112 | 4/1993 | Prencipe et al. | 526/271 |
| 5,300,283 | 4/1994 | Prencipe et al. | 524/52 |

FOREIGN PATENT DOCUMENTS

| | | | |
|---|---|---|---|
| 0068847 | 5/1987 | European Pat. Off. | 526/271 |
| 1285208 | 8/1972 | United Kingdom | C08F 15/40 |

*Primary Examiner*—Thurman K. Page
*Assistant Examiner*—Peter F. Kulkosky
*Attorney, Agent, or Firm*—M. M. Grill; R. L. Stone; R. J. Ancel

[57] ABSTRACT

A personal care composition in the form of a hair or skin-treating gel containing an amount of a synthetic linearly viscoelastic cross-linked polymeric thickening agent, especially a cross-linked methyl vinyl ether/-maleic anhydride copolymer, effective to render the composition linearly viscoelastic, and a method of promoting personal care by applying an effective amount of the composition to the hair or skin.

15 Claims, No Drawings

VISCOELASTIC PERSONAL CARE COMPOSITION

This application is a continuation-in-part of application Ser. No. 07/738,766 filed Aug. 1, 1991, and now U.S. Pat. No. 5,202,112.

This invention relates to novel aqueous personal care compositions, especially to hair and skin treating gels having viscoelastic properties.

A thickening agent (binding or gelling agent) is commonly employed in personal care compositions to prevent separation of ingredients in storage, promote dispensability and retention in use as on local topical locations, improve cosmetic properties and the like. Such thickeners are most often hydrophilic colloids which disperse in aqueous media. Some widely used thickeners are cellulose derivatives because they are cheap and their quality can be closely controlled. Sodium carboxymethyl cellulose (NaCMC) is illustrative, but compositions thickened therewith are often subject to syneresis, i.e. phase separation and severe loss of rigidity and viscosity. It is believed that this may be caused partly by enzymatic degradation of the NaCMC by cellulytic enzyme (cellulase) which can be produced by moulds and bacteria present in some batches of NaCMC. These microorganisms may originate in the water, or on storage of the NaCMC, in damp conditions which support growth, or from other sources of contamination. Killing the organism responsible does not, of course, remove the enzyme already produced.

Hydroxyethyl cellulose is a thickener with a better resistance to cellulytic attack than NaCMC, possibly due to its more uniform substitution pattern along the molecule compared with NaCMC, but in personal care formulations, it often produces a product with an unacceptably "long" or "stringy" texture.

The prior art also proposes the use of carboxyvinyl polymers as thickeners. The carboxyvinyl polymers are colloidally water soluble polymers of acrylic acid cross-linked with about 0.75% to 2.0% of polyallyl sucrose or polyallylpentaethrythritol, obtainable under the Carbopol trademark from B. F. Goodrich. It is known, however, that Carbopol is hard to disperse. The problem arises because Carbopol is so hydrophilic that the individual particles swell and the particles clump to form aggregates. When dispersion is attempted, the outside of the aggregate hydrates and swells. The inside is no longer readily contacted with water. This causes fish eyes and regions of inhomogeneity that are very hard to remove by further mixing. The fish eyes and nonhomogenous dispersion persist in the final product. The result is decreased control over the final rheological properties of the product and increased batch to batch variation. These variations are readily perceived by the end user and are interpreted as poor quality product.

In general, composition thickened with vegetable thickeners, for example alginates, carageenates, gum arabic and cellulose derivatives such as methylcellulose, hydroxymethylcellulose, hydroxyethylcellulose, hydroxyl propylcellulose, hydroxypropylmethylcellulose and carboxylmethylcellulose frequently are relatively unstable on storage.

Many consumers prefer gels to non-viscous liquids because of the impression of strength conveyed as well as other aesthetic properties. Moreover, gels can be dispensed by methods other than by simple pouring such as from flexible or deformable squeeze tubes, dipping from open jars and other containers, etc.

It is an object of this invention to provide personal care compositions which will not be subject to the aforementioned deficiencies. Another object of this invention is the provision of a linear viscoelastic personal care composition. Still another object of this invention is the provision of a linear viscoelastic personal care composition having excellent stability against phase separation or syneresis, viscosity change in storage, and settling of dissolved, dispersed or suspended particles under high and low temperature conditions, freedom from fish eyes, excellent texture and other cosmetic properties, ease of extrusion from a dispensing tube, pump or the like (easily shear thinned), and good stand-up after extrusion (quick recovery of structure). A further object of this invention is the provision of a method for promoting personal care hygiene by applying to the hair and skin, including the scalp, an effective amount of the compositions of this invention. Other objects and advantages will appear as the description proceeds.

This invention enables the provision in aqueous gel form of substantially all types of personal care or cosmetic compositions for topical treatment of, or application to, hair and skin (of animals, preferably human, and preferably living), for example including hand, facial and scalp cleansers, shampoos, antiperspirants, deodorants, skin conditioners, moisturizers, refreshers, softeners, wrinkle, itch, blemish and acne reducers and inhibitors, sun screens, insect repellents, topical analgesics, antiseptics and wound protectants, shave and after shave preparations, hair conditioners, colorants, rinses and fixatives, foam baths and the like.

In accordance with certain of its aspects the attainment of the objects of this invention is realized by the provision of a linear viscoelastic personal care composition in the form of a hair or skin treating gel preferably with a pH of about 4 to about 9, comprising a topically acceptable aqueous vehicle, and, in an amount effective to render the composition linearly viscoelastic, a synthetic linearly viscoelastic cross-linked polymeric thickening agent having in a 1 wt. % aqueous solution an elastic or storage modulus $G'$ and a viscous or loss modulus $G''$ substantially independent of frequency in an applied frequency range of 0.1 to 100 radiants/sec, a $G'$ minimum value of 1,000 dynes/sq.cm. which varies less than 1 order of magnitude of its original value, and a ratio of $G''/G'$ ranging from more than 0.05 to less than 1.

The linear viscoelastic aqueous personal care compositions of this invention will, at least in the preferred embodiments, satisfy each of the following stability criteria over the aging temperature-time schedule shown by the following Table A:

TABLE A

| Aging Temperature (°F.) | Minimum Duration (Weeks) |
|---|---|
| 120 | 9 |
| 100 | >12 |
| 77 | >52 |

More specifically, the compositions are considered stable if each of the following stability criteria is satisfied for at least the minimum number of weeks for each aging temperature shown in Table A:

a. no significant visible phase separation (i.e. no solid/liquid separation)

b. no significant change in viscosities, yield, stress or other dynamic-mechanical properties, c. no discolorization or significant color change As used herein, "linear viscoelastic" means that the elastic (storage) modulus (G') and the viscous (loss) modulus (G") of the composition are both substantially independent of strain, at least in an applied strain range of from 0–10%. Dynamic oscillatory measurements are performed using the Rheometrics System Four instrument. In this experiment an oscillatory shear field is imposed on the material, and the corresponding shear stress response is measured. The stress is defined by a component in phase with the displacement (elastic modulus, G') and a component 90° out of phase (loss modulus, G"). The value of G' indicates the degree of elasticity and network formation in the system; see 1. Menjivar, J. A., "Water Soluble Polymers; Beauty with Performance"; Glass, J. E., Ed; Advances in Chemistry 213; American Chemical Society, Washington, D.C. 1986, pp 209–226; and
2. Sinton, S.; Maerker, J.; J. Rheol. (NY) 1986 30 77, both incorporated herein by reference.

More specifically, a personal care composition is considered to be linear viscoelastic for purposes of this invention, if over the strain range of 0–50% the elastic modulus G' has a minimum value of 1000 dynes/sq.cm., and varies less then about 1 order of magnitude of its original value. Preferably, the minimum value of G' and maximum variation of G' applies over the strain range of 0.1 to 50%.

As a further characteristic of the preferred linear viscoelastic personal care compositions the ratio of G"/G' (Tan δ) is less than 1, preferably less than 0.8, but more than 0.05, preferably more than 0.2, at least over the strain range of 0 to 50%. It should be noted in this regard that % strain is shear strain $\times 100\%$.

With respect to 1 wt. % aqueous solutions of the required cross-linked polymer, elastic moduli G' substantially independent of frequency and higher than the corresponding loss moduli G" indicate solid-like behavior characteristic of gel structure: see 3. Prud'homme, R. K.; Constien, V., and Knoll, S.; "Polymers in Aqueous Media"; Glass, J. E., Ed; Advances in Chemistry 223; American Chemical Society, Washington, D.C., 1989, pp. 89–112, also incorporated herein by reference.

In such solutions, more specifically, G' and G" are substantially independent of frequency in an applied frequency range of 0.1 to 100 radiants/sec, G' has a minimum value of 5,000 dynes/sq.cm. which varies less than 1 order of magnitude of its original value, and the ratio G"/G' ranges from more than 0.05 to less than 1;

By way of further explanation, the elastic (storage) modulus G' is a measure of the energy stored and retrieved when a strain is applied to the composition, while viscous (loss) modulus G" is a measure of the amount of energy dissipated as heat when strain is applied. Therefore, a value of Tan δ corresponding to:

$0.05 < \text{Tan}\delta < 1$, preferably $0.2 < \text{Tan}\delta < 0.8$ means that the compositions will retain sufficient energy when a stress or strain is applied, at least over the extent expected to be encountered for products of this type, for example, when squeezed out of a tube or pump to return to its previous condition and exhibit excellent stand-up when the stress or strain is removed. The compositions with Tan δ values in these ranges, therefore, will also have a high cohesive property, namely, when a shear or strain is applied to a portion of the compositions to cause it to flow, the surrounding portions will follow. As a result of this cohesiveness of the linear viscoelastic characteristic, the compositions will readily flow uniformly and homogeneously from a pump or tube when it is squeezed thereby contributing to the stand-up and ease of extrusion properties which characterize the compositions of this invention. The linear viscoelastic property also contributes to improved physical stability against phase separation of suspended particles by providing a resistance to movement of the particles due to the strain exerted by a particle on the surrounding fluid medium.

From another aspect, a desirable rheological property which the cross-linked polymers employed herein display in solution which indicates gel network formation is the presence of a yield point. Yield point is defined as the amount of shear stresses needed to initiate flow; see 4. Goodwin, J. W., "Solid/Liquid Dispersions"; Tadros, Th. F., Ed; Academic Press, N.Y., 1987, pp 199–224, also incorporated herein by reference. At shear stress values lower than the yield point, no flow occurs. This plastic rheology is desirable because when the gel displays a sufficiently high yield value it allows permanent suspensions of particles that are formulated in the gel. This is especially important in hand cleaners, where suspension of abrasive particles is necessary. See
5. Lockhead, R. Y., Davidson, J. A., and Thomas, G. M.; "Polymers in Aqueous Media: Performance Through Association"; Glass, J. E., Ed; Advances in Chemistry 223; American Chemical Society, Washington, D.C., 1989, pp 113–147, also incorporated herein by reference.

The above-described linear viscoelastic properties of the personal care compositions of this invention are fundamentally provided by the defined synthetic linearly viscoelastic crosslinked polymeric thickening agents which generally have a molecular weight (M.W.) of about 1,000 to about 5,000,000. The homopolymers and copolymers (from 2, 3 or more monomers) to be cross-linked are generally anionic comprising a chain or backbone containing repeating units each preferably containing at least one carbon atom (typically only carbon atoms in the chain or backbone) and preferably at least one directly or indirectly pendant monovalent acidic group, e.g. sulfonic, phosphinic, or preferably phosphonic or carboxylic, or salt thereof, e.g. alkali metal or ammonium. It is ordinarily desirable that the repeating units constitute at least about 10%, preferably at least about 50%, more preferably at least about 80% up to 95% or 100% by weight of the polymer. Preferably, about 0.1 to about 2.5% of the crosslinked polymer is employed in the personal care compositions herein.

According to a preferred embodiment, the required crosslinked polymer is derived from a synthetic anionic polymeric polycarboxylate, many types of which are disclosed in the prior art, for example, as anticalculus agents in U.S. Pat. No. 3,429,963 to Shedlovsky; U.S. Pat. No. 4,152,420 to Gaffar; U.S. Pat. No. 3,956,480 to Dichter et al; U.S. Pat. No. 4,138,477 to Gaffar; and U.S. Pat. No. 4,183,914 to Gaffar et al.

These synthetic anionic polymeric polycarboxylates are often per se employed in the form of their free acids or preferably partially or more preferably fully neutralized water soluble or water swellable (hydratable, gel/-forming) alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether/maleic anhydride (MVE/MA) having a molecular weight (M.W.) of about 30,000 to about 1,000,000. These copolymers are available, for example, as Gantrez e.g. AN 139 (M.W. 500,000), AN 119 (M.W. 250,000); and S-97 Pharmaceutical Grade (M.W. 70,000), of GAF Corporation. Also useful are terpolymers such as 1.0 MA/0.4 MVE/0.1 dodecane, 1.0 MA/0.75 MVe/0.25 decene, 1.0 MA/0.95 MVE/0.05 eicosene or tetradecene, 1.0 MA/0.9 MVE/0.1 tetradecene, 1 MA/0.9 MVE/0.1 acrylic acid, vinylpyrrolidone or isobutane.

Other operative polymeric polycarboxylates include those disclosed in U.S. Pat. No. 3,956,480 referred to above, such as the 1:1 copolymers of maleic anhydride with ethyl acrylate, hydroxyethyl methacrylate, N-vinyl-2-pyrollidone, or ethylene, the latter being available, for example, as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrollidone.

Additional operative polymeric polycarboxylates disclosed in above referred to U.S. Pat. No. 4,138,477 and 4,183,914, include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorosorbic, cinnamic, beta-styrylacrylic, muconic, iraconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers ordinarily contain sufficient carboxylic salt groups for water-solubility.

The synthetic anionic polymeric polycarboxylate component is most often a hydrocarbon with optional halogen and O-containing substituents and linkages as present in, for example, ester, ether and OH groups.

According to another preferred embodiment of this invention, the required cross-linked polymer is derived from a polymer containing repeating units in which one or more phosphonic acid groups are bonded to one or more carbon atoms in the polymer chain. Examples of such polymers are poly (vinyl phosphonic acid) containing units of the formula:

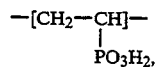

a copolymer having units of vinyl phosphonic acid of formula I alternating or in random association with units of vinyl phosphonyl fluoride, poly(1-phosphonopropene) with units of the formula:

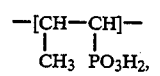

poly (beta styrene phosphonic acid) containing units of the formula:

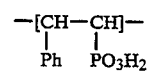

wherein Ph is phenyl, a copolymer of beta styrene phosphonic acid with vinyl phosphonic acid having the units of formula III alternating or in random association with units of Formula I above and poly (alpha styrene phosphonic acid) containing units of the formula:

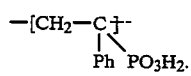

These styrene phosphonic acid polymers and their copolymers with other inert ethylenically unsaturated monomers generally have molecular weights in the range of about 2,000 to about 30,000, preferably about 2,500 to about 10,000. Such "inert" monomers are those which do not significantly interfere with the intended function of the cross-linked polymer.

Other phosphonic-containing polymers include, for example, phosphonated ethylene having units of the formula.

where may, for example, be an integer or have a value giving the polymer a molecular weight of about 3,000; sodium poly (butene-4,4-diphosphonate) having units of the formula:

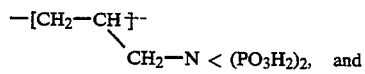

poly (allyl bis (phosphonoethyl amine) having units of the formula:

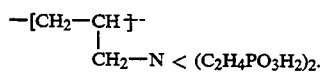

Still other phosphonated polymers include, for example, poly (allyl phosphono acetate), phosphonated polymethacrylate, etc. and the geminal diphosphonate polymers disclosed in EP Publication 0321233.

As illustrative of polymers containing phosphinic acid and/or sulfonic acid groups, there may be mentioned polymers and copolymers containing units or moieties derived from the polymerization of vinyl or allyl phosphinic and/or sulfonic acids. Mixtures of these monomers may be employed, and copolymers thereof with one or more inert polymerizable ethylenically unsaturated monomers such as those described above with respect to the operative synthetic anionic polymeric polycarboxylates. As will be noted, in these and other crosslinkable polymers for use herein, usually only one acidic group is bonded to any given carbon or other atom in the polymer backbone or branch thereon. Polysiloxanes containing or modified to contain pendant acidic groups may also be employed herein. Also effective are ionomers containing or modified to contain acidic groups. Ionomers are described on Pages 546–573 of the Kirk-Othmer Encyclopedia of Chemical Technology, third edition, Supplement volume, John Wiley and Sons, Inc. copyright 1984, which description is incorporated herein by reference. Also effective, provided they contain or are modified to contain acidic groups, are polyesters, polyurethanes and synthetic and natural polyamides including proteins and proteinaceous materials such as collagen, poly (arginine) and other polymerized amino acids.

The cross-linkable polymers and copolymers described above can contain moieties in the chain or backbone derived from polymerizable ethylenically unsaturated monomers in addition to and different from the described acidic group-containing monomeric moieties. Polymerization is conducted in known manner, often in the presence of an initiator, and preferably by slurry polymerization in a solvent medium in which the monomers but not the polymer products are soluble or readily dispersible.

For purposes of this invention, the above-described polymers must be cross-linked to be linearly viscoelastic. The polymers are lightly cross-linked so that they swell and form gels, strong three-dimensional networks in aqueous systems. Excessive cross-linking leading to hard, irreversible polymers is to be avoided. The amount of cross-linking agent can vary from about 0.01 to about 30 wt. % of the total, cross-linked polymer, preferably about 2 to about 20 wt. %, more preferably about 3 to about 15 wt. %.

According to a preferred embodiment, cross-linking is carried out concurrently during polymerization of the monomeric components of the polymer by including therein the requisite amount of cross-linking agent. In this embodiment, the cross-linking agents are typically hydrocarbons of at least 4, preferably at least 5, up to about 30, carbon atoms containing 2, less preferably 3 or more, polymerizable activated ethylenically unsaturated groups preferably in non-conjugated, terminal relationship. They can contain optional halogen and/or oxygen-containing substituents and linkages such as ester, ether and OH groups. Examples of such cross-linking agents include 1, 7-octadiene, 1, 9-decadiene, 1, 5-hexadiene, divinyl glycol, butanediol divinyl ether, N,N'-methylenebisacrylamide, polyethylene glycol diacrylates and dimethacrylates which in each case are derived from polyethylene glycol with a molecular weight of 126 to 8500, trimethylolpropane triacrylate and trimethyacrylate, ethylene glycol, propylene glycol, butanediol, hexanediol and dodecanediol diacrylates and dimethacrylates, the diacrylates and dimethacrylates of block copolymers derived from ethylene oxide and propylene oxide, multivalent alcohols (e.g. glycerol, sucrose or pentaerythritol) di- or triesterified with acrylic acid or methacrylic acid, triallylamine, tetraallylethylenediamine, divinylbenzene, diallyl phthalate, polyethylene glycol divinyl ether, trimethylolpropane diallyl ether, polyallyl sucrose and pentaerythritol, and divinylethylene urea and mixtures thereof.

U.S. Pat. No. 5,034,488 to Tazi et al (GAF) discloses a concurrent cross-linking process as described above in the production of cross-linked copolymers of maleic anhydride and an alkyl vinyl ether such as methyl vinyl ether operative herein as a synthetic linearly viscoelastic crosslinked polymeric thickening agent employed in the personal care compositions of this invention.

According to another embodiment, cross-linking can be achieved after the cross-linkable polymer is formed (postpolymerization) by reaction with amounts of polyfunctional cross-linking agents reactive with corresponding amounts of pendant reactive groups along the polymer chain, e.g. OH, $NH_2$, $CONH_2$ and especially the aforementioned acidic (e.g. carboxylic, phosphonic, phosphinic, sulfonic, etc.) groups in the polymer. Crosslinking agents reactive with the acidic groups usually contain at least about 4 up to about 30 carbon atoms and may include, for example, linear and cyclic polyols such as butane and octadecane diols, polyethylene glycol, glycerol, sucrose and pentaerythritol, and the corresponding polythiols and polyamines such as hexamethylene and octadecane diamines and the like. Cross-linking agents reactive with other of the aforesaid pendant reactive groups include the corresponding polyfunctional acidic compounds, e.g. containing at least 2 of the foresaid acidic groups such as butane, decane and octadecane dicarboxylic acids. Post-polymerization is usually less preferred since the resulting cross-linked products often tend to be more easily subject to hydrolysis or the like with resulting loss of the desired linearly viscoelastic properties.

It will be understood that for post-polymerization cross-linking of maleic anhydride-containing polymers and copolymers, the anhydride ring must first be opened by hydrolysis to release the free -COOH groups needed for reaction with the cross-linking agent.

The aqueous vehicle in the personal care compositions of this invention usually comprises about 30% to about 98% of water and may include other onventional liquid excipients of personal care compositions such as humectants, water soluble or insoluble liquid emollients, organic liquid solvents and the like.

Non-toxic, humectants suitable for optional use in amounts of about 1 to about 15% in these personal care compositions include, for example, sorbitol (usually in the form of a 70% aqueous solution), glycerine, propylene glycol, xylitol, polypropylene glycol and/or polyethylene glycol (e.g. 400–600), especially mixtures of glycerine and sorbitol. In clear gels where the refractive index is an important consideration, a mixture of about 0 to about 80% of glycerine and about 20 to about 80% of sorbitol with about 3 to about 30% of water is preferably employed.

Personal care cleansing compositions of this invention may contain a dermatologically acceptable abrasive or polishing material in conjunction with surfactants, liquid organic solvents and the like. Examples of such abrasive materials in the form of water insoluble finely divided particles are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, aluminum silicate, zirconium silicate, silica, bentonire, pumice, calcite and mixtures thereof. Other suitable polishing materials include the particulate thermosetting resins described in U.S. Pat. No. 4,070,510 of Dec. 15, 1962 such as melamine-, phenolic-, and urea-formaldehydes, and cross-linked polyepoxides and polyesters. Preferred polishing materials include pumice, calcite, crystalline silica having particle sizes of up to about 5 microns, a mean particle size of up to about 1.1 microns, and a surface area of up to about 50,000 cm.$^2$/gm., silica gel or colloidal silica, and complex amorphous alkali metal aluminosilicate.

It will be understood that other conventional thickeners (binding, gelling agents) may be included in these personal care compositions, usually in amounts ranging from about 0.1 to about 4 parts per part by weight of the defined cross-linked polymeric thickener. Examples of such other thickeners include xanthan gum, hydroxyethyl cellulose and water-soluble salts of cellulose ethers such as sodium carboxymethyl cellulose and sodium carboxymethyl hydroxyethyl cellulose. Natural gums such as carrageenan (Irish moss, Viscarin), gum karaya, gum arabic, and gum tragacanth can also be used. Colloidal magnesium aluminum silicate, Veegum or finely divided silica can be used as part of the thickening agent system. Preferred thickening agents include xanthan gum, carrageenan, sodium carboxymethyl cellulose, sodium carboxymethyl hydroxyethyl cellulose and hydroxyethyl cellulose, preferably in proportions of about 0.4 to about 3 parts per part of the cross-linked polymeric thickener. Also useful is synthetic hecterite, a synthetic colloidal magnesium alkali metal silicate complex clay available for example as Laponite (e.g. CP, SP 2002, D) marketed by Laporte Industries Limited. Laponite D analysis shows, approximately by weight, 58.00% SiO$_2$, 25.40% MgO, 3.05% Na$_2$O, 0.98% Li$_2$O, and some water and trace metals. Its true specific gravity is 2.53 and it has an apparent bulk density (g./ml. at 8% moisture) of 1.0.

Other suitable thickeners include starch, polyvinylpyrrolidone, hydroxybutyl methyl cellulose, hydroxypropyl methyl cellulose, alginates, gum ghatti, locust bean gum, pectens, and tamarind gum and the like.

It will be understood that, as is conventional, the preparations are to be sold or otherwise distributed in suitable labelled packages in a wide-mouth jar, collapsible tube, typically aluminum, lined lead or plastic, or other squeeze or pump dispenser for metering out the contents, having a label describing it, in substance, as a hand cleaner, moisturizer, conditioner, hair fixative or the like.

Organic surface-active agents (surfactants) are used in most compositions of the present invention to achieve increased prophylactic and detersive action, assist in achieving thorough and complete dispersion of the ingredients in the squeous vehicle, facilitate and expedite contact with the skin or hair, and render the instant compositions more cosmetically acceptable. The organic surface-active material is preferably anionic, non-ionic or amphoteric in nature. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material.

Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic materials).

Examples of amphoteric surfactants useful herein include alkylamino-mono-and-di-propronates, betaines such as N-alkylbetaines, N-alkylsulphobetaines and N-alkylamido-betaines, cycloimidinium compounds such as alkylimidazoles, and asparagine derivatives.

The alkyl groups in these surfactants may contain 1 to about 22, preferably about 10 to about 20, carbon atoms. These surfactants are in general included in amounts from about 0.1% to about 15%, more usually about 0.2% to about 5%.

Various other materials may be incorporated in the personal care preparations of this invention such as whitening agents, pigments, dyes, fragrances, pH controllers, foam improvers and stabilizers, opacifiers, sequestering, opacifying agents, preservatives, silicones, chlorophyll compounds, superfatting agents, antiseptics, solvents, sunscreens, oxidizing and reducing agents, antidandruff and/or ammoniated material such as urea, diammonium phosphate, and mixtures thereof. The adjuvants, where present, are incorporated in the preparations in amounts such as 0.01% to 15% which do not significantly adversely affect the properties and characteristics desired.

Many types of personal care compositions contain emollients which may be water-solube or insoluble, solid or waxy (with melting points between about 20° C. and 65° C. or liquid or oily at ambient temperatures. Examples of such emollients include polyhydric alcohols, polyether derivatives, hydrocarbon oils and waxes, triglyceride esters, acetoglyceride esters, ethoxylated glycerides, alkene and alkyl esters of carboxylic acids, higher fatty acids, alcohols, alcohol ethers and ether esters, lanolin and its derivatives, polyhydric alcohol esters, wax esters, beeswax and vegetable waxes and derivatives, phospholipids, sterols, fatty acid amides and its derivatives, as described in Column 3, Lines 20 to 50, and Column 6, Line 1 to Column 7, Line 11 of U.S. Pat. No. 4,478,853. The latter patent also describes other conventional excipients of personal care compositions at column 8, Lines 1-33. Said descriptions are incorporated herein by reference thereto. These emollients may in general be employed in amounts from about 2% to about 80%, more usually about 5% to about 60%.

Exemplary hair setting gels may contain, approximately by weight, 60% to 98% of water, 0.01% to 5% of a hair setting polymeric material, 0.1% to 5% of a nonionic, anionic or amphoteric surfactant or mixture thereof, and 0.02% to 5% of the above described crosslinked polymeric thickening agent containing at least about 3% of cross-linking agent. The hair setting polymeric material may be any conventionally employed anionic, nonionic or amphoteric polymer, including any of the abovedescribed polymers, crosslinked or non-crosslinked, and generally in amounts similar to those of the described crosslinked polymeric thickening agents.

Exemplary skin lotion gels may contain, approximately by weight, 60% to 90% of water, 0.1% to 5% of a nonionic, anionic or amphoteric surfactant or mixture thereof, 5% to 35% of a solid emollient material, and 0.02% to 5% of the above described crosslinked polymeric thickening agent containing at least about 3% of cross-linking agent.

Exemplary skin cream gels may contain, approximately by weight, 40% to 60% of water, 0.1% to 5% of a nonionic, anionic or amphoteric surfactant or mixture thereof, 10% to 40% of liquid emollient material, 10% to 30% of solid emollient material, and 0.02% to 5% of the above described crosslinked polymeric thickening agent containing at least about 3% of crosslinking agent.

Exemplary hair skin cleaner gels may contain, approximately by weight, 50% to 70% of water, 0.1% to 5% of a nonionic, anionic or amphoteric surfactant or mixture thereof, 5% to 20% of a dermatologically acceptable skin abrasive, and 0.02% to 5% of the above described crosslinked polymeric thickening agent containing at least about 3% of crosslinking agent.

The following Examples A-F illustrate the preparation of operative synthetic cross-linked polymers and their properties. All parts, amounts and proportions referred to herein and in the appended claims are by weight, and temperatures are in degrees C unless otherwise indicated.

| Post Polymerization Cross-Linking | | |
|---|---|---|
| | Example A | Example B |
| PVM/MA * | 0.33330 Moles | 0.33001 Moles |
| PEG 600 ** | 0.00166 Moles | 0.00249 Moles |
| MEK *** | 6.6 | 6.6 |

* Gantrez AN139, vinylmethyl ether/maleic anhydride 1/1 copolymer M.W. 500,000 (GAF Corp.).
** Polyethylene glycol, M.W 600 (13–14 E.O.)
*** Methyl ethyl ketone The PVM/MA copolymer is dissolved in the MEK (b.pt. 80° C.) yielding a 10 wt. % solution, in a stirred 1 liter resin kettle. The PEG is then added and the liquor refluxed for about 4 hours. At least 400 ml. of MEK are collected by distillation through a cold water condenser. A pink viscous syrup results which is poured at 50°–60° C. into a large evaporating dish and further devolatized under vacuum at 60°–70° C. overnight.

Though the starting PVM/MA copolymer is both ketone-soluble and water-soluble to a high degree, the products of both Examples A and B are pink, very hard solids, only slightly soluble in ketones, and insoluble but rapidly swelling in water to form gels. I.R. spectrum analyses show that the starting polymer has no free —COOH groups but both products show strong —COOH peaks resulting from ring opening and ester cross-links, indicative of an Example A product containing about 0.5 mole % or about 2 wt. % of PEG cross-linkages and an Example B product containing about 0.75 mole % or about 3 wt. % of PEG cross-linkages.

Concurrent Cross-Linking Polymerization

Example C

In a one liter pressure reactor are charged the following: 404.4 parts cyclohexane, 269.6 parts ethyl acetate, and 6 parts 1,7 octadiene. 0.3 Parts of the initiator t-butylperoxypavilate are added at 58° C. in three increments of 0.1 part each at times: 0, 60, and 120 minutes from the first addition. Seventy-five parts of molten maleic anhydride and 49.0 parts of methyl vinyl ether are mixed together and gradually added to the reaction vessel at 58° C. and 65 psi (natural pressure of the system) over a 2 hour period of time. The reaction mixture is then held at 58° C. for two hours after the last addition of initiator. The presence of maleic anhydride is followed by testing with triphenyl phosphene until testing is negative. The product precipitates out of solution (slurry polymerization). After the reaction is complete, the product is cooled to room temperature, filtered and dried in a vacuum oven. It is a 1:1 cross-linked copolymer of methyl vinyl ether and maleic anhydride (PVM/MA) containing about 4.6 wt. % of the octadiene cross-linking agent.

Example D

The procedure of Example C is repeated using 5 parts of 1,9-decadiene instead of the 6 parts of 1,7-octadiene. The product, in the form of a white powder, has the following viscosity specifications in varying concentrations in aqueous solution at pH 7 and 25° C. by Brookfield RVT, Spindle TC at 10 RPM:

TABLE 1

| Concentration | Viscosity |
|---|---|
| 0.25% | 30,800 cps |
| 0.50% | 63,500 cps |
| 1.00% | 90,000 cps |

An 0.5% aqueous solution of this product, pH adjusted to 7, has the following viscosity properties when measured with a Brookfield Model RVT, Spindle TC, at varying RPM's:

TABLE 2

| RPM | Viscosity |
|---|---|
| 1 | $376 \times 10^3$ |
| 2.5 | $180 \times 10^3$ |
| 5 | $105 \times 10^3$ |
| 10 | $59 \times 10^3$ |

These results show that even at very low concentrations this cross-linked PVM/MA copolymer yields highly viscous solutions.

The following yield points of varying concentrations of this polymer in aqueous solution at pH 7 are obtained using the Haake Rotoviscometer RV12 with MV IP sensor system and shear rates varied from 0 to 10 sec−1:

TABLE 3

| Concentration | Yield Point (Pascals) |
|---|---|
| 0.125 | 37 |
| 0.250 | 64 |
| 0.500 | 180 |

These high-yield points, corresponding to the amount of shear stress needed to initiate flow, indicate gel network formation enabling permanent stabilization of suspensions of particles such as insoluble polishing materials in some personal care compositions and other suspended particles.

Example E

One percent aqueous solutions of cross-linked PVM/MA copolymer containing from 0.01% to 10% of 1,7-octadiene cross-linking agent, prepared as described in Example C, are shaken overnight in order to hydrolyze the maleic anhydride ring and then neutralized with NaOH to fully ionize the carboxyl groups. The results listed in the following table indicate that solutions containing more than 2.5%, i.e. at least about 3% of cross-linking agent gel whereas solutions containing up to 2.5% cross-linking agent do not gel.

TABLE 4

| Wt. % Cross-Linking Agent | Gelling Results |
| --- | --- |
| 0.1 | No gel |
| 0.5 | No gel |
| 1.0 | No gel |
| 2.5 | No gel |
| 5.0 | Gelled |
| 7.5 | Gelled |
| 10.0 | Gelled |

Optional Hydrolysis Procedure

Example F

To a 2 liter kettle fitted with a mechanical agitator and a reflux column add 962 grams of deionized water and 28 grams of a 10% aqueous sodium hydroxide solution. Heat to 65° C. and add 10 grams of the product of Example D with stirring. The system becomes clear within 2 hours and has a pH of about 7. The resultant gel has a solids content of 1%.

The following examples are only illustrative of the personal care compositions of this invention. Typically, the cross-linked polymer or copolymer is hydrolyzed in water for 2 to 3 days at an appropriate solids concentration varying from about 5 to 10% polymer content, neutralized to pH 7, the mixture dispersed in the humectant system, and the resulting dispersion mixed with the other ingredients at a pH of about 7. The crosslinked polymer ("XL Polymer") in these formulations may be crosslinked PVM/MA of Example A containing about 0.5 mole % of PEG 600 crosslinking agent, crosslinked PVM/MA of Example C containing about 5 wt. % of 1,7-octadiene crosslinking agent, or crosslinked PVM/MA of Example E containing about 10% of 1,7-octadiene crosslinking agent.

The products of Examples 1-4 all have the desired viscoelastic properties described above.

EXAMPLE 1

| Hair Setting Gel | |
| --- | --- |
| Ingredients | Weight % |
| XL Polymer | 1.0 |
| PVP/VA* | 0.5 |
| Tween 80** | 0.3 |
| Fragrance | 0.19 |
| FD&C Yellow #5 | 0.001 |
| Water, Q.S. to | 100 |

*Poly (vinyl pyrollidone/vinyl acetate), GAF Corp., hair setting agent.
**Oleate esters of sorbitol and sorbitol anhydrides, ICI U.S., surfactant, emulsifier.

Make a 1% by weight slurry with water of the anhydrous XL polymer. Allow polymer to fully hydrate (24-72 hrs.) while continuously shaking the mixture. To the resultant polymer solution, add the PVP/VA copolymer and blend well until dispersed. Neutralize the blend with NaOH (50% solution) until gel forms. Add Tween 80 and fragrance. To the final product, FD&C Yellow #5 dye is added to improve its appearance. Neutralization with NaOH can also be performed after addition of the surfactant, fragrance, and color.

EXAMPLE 2

| Hand Lotion Gel | |
| --- | --- |
| Ingredients | Weight % |
| XL Polymer | 1.0 |
| Methylparaben | 0.15 |
| Imidazolidinyl Urea | 0.2% |
| Tetrasodium EDTA | 0.05 |
| Glyceryl Stearate S.E. | 2.0 |
| Cetyl Alcohol | 2.0 |
| Sorbitan Stearate | 2.1 |
| Polysorbate 60* | 2.9 |
| BHT** | 0.1 |
| Cocoa Butter | 10.0 |
| Triethanol Amine 99% | 0.54 |
| Deionized Water. Q.S. to | 100 |

*Polyoxyethylene (20) sorbitan monostearate
**Butylated hydroxytoluene.

EXAMPLE 3

| HAND CLEANER GEL | |
| --- | --- |
| Ingredients | Weight % |
| XL Polymer | 1.0 |
| Odorless Mineral Spirits | 29.0 |
| Lanolin USP | 0.5 |
| Petrolatum | 0.5 |
| Pumice, Talc or Calcite Powder | 10.0 |
| Triethanolamine (99%) | 0.3 |
| PEG-15 Cocamine* | 0.3 |
| Deionized Water, Q.S. to | 100 |

*Polyethylene glycol (15) coconut amine

EXAMPLE 4

| MOISTURIZING SKIN CREAM GEL | |
| --- | --- |
| Ingredients | Weight % |
| XL Polymer | 0.7 |
| Liquid Paraffin (70) | 25.0 |
| Jojoba wax | 10.0 |
| Ceresin | 2.0 |
| Beeswax | 8.0 |
| Lanolin Wax | 1.5 |
| Glyceryl Stearate | 3.5 |
| Ceteth-16* | 2.0 |
| Triethanolamine 99% | 0.43 |
| Fragrance | Q.S. |
| Deionized Water, Q.S. to | 100 |

*Polyethylene glycol (16) cetyl ether.

This invention has been described with respect to certain preferred embodiments and it will be understood that modifications and variations thereof obvious to those skilled in the art are to be included within the spirit and purview of this application and the scope of the appended claims.

We claim:

1. A linear viscoelastic personal care composition in the form of a hair or skin-treating aqueous gel with a pH of about 4 to about 9 comprising a topically acceptable aqueous vehicle, about 0.01% to 5% of a nonionic, anionic or amphoteric surfactant or mixture thereof and, in an amount of about 0.02% to 5 weight % effective to render the composition stable against phase separation or syneresis, viscosity change in storage, settling of dispersed or suspended particles under high and low-temperature conditions and formation of fish eyes, highly cohesive, readily flowable uniformly and homogeneously when extruded from a dispensing tube or pump with excellent subsequent stand-up and return to its pre-extrusion condition, and linearly viscoelastic, a synthetic linearly viscoelastic cross-linked polymeric thickening agent having in a 1 wt. % aqueous solution an elastic or storage modulus $G'$ and a viscous or loss modulus $G''$ substantially independent of frequency in an applied frequency range of 0.1 to 100 radians/sec, a $G'$ minimum value of 1,000 dynes/sq. cm which varies less than 1 order of magnitude of its original value, and a ratio of $G''/G'$ ranging from more than 0.05 to less than 1, said thickening agent having a molecular weight of about 1,000 to about 5,000,000 and containing about 0.01 to about 30% of cross-linking agent by weight of the cross-linked thickening agent.

2. A composition according to claim 1 containing approximately by weight, 30 to 98% of water, in said cross-linked polymeric thickening agent containing at least about 3% of crosslinking agent.

3. A composition according to claim 1 in the form of a hair setting gel containing, approximately by weight, 60% to 98% of water, 0.01% to 5% of a hair setting polymeric material, in said cross-linked polymeric thickening agent containing at least about 3% of cross-linking agent.

4. A composition according to claim 1 in the form of a skin lotion gel containing, approximately by weight, 60% to 90% of water, 0.1% to 5% of a nonionic, anionic or amphoteric surfactant or mixture thereof, in 5% to 35% of solid emollient material, said cross-linked polymeric thickening agent containing at least about 3% of cross-linking agent.

5. A composition according to claim 1 in the form of a moisturizing skin cream gel containing, approximately by weight, 40% to 60% of water, 0.1% to 5% of a nonionic, anionic, or amphoteric surfactant or mixture thereof, 10% to 40% of liquid emollient material, in 10 to 30% of solid emollient material, said cross-linked polymeric thickening agent containing at least about 3% of cross-linking agent.

6. A composition according to claim 1 in the form of a hand skin cleaner gel containing about 50% to 70% of water, 20% to 40% of a liquid organic solvent, 0.1 to 5% of a nonionic, anionic or amphoteric surfactant or mixture thereof, in 5% to 20% of a dermatologically acceptable skin abrasive, said cross-linked polymeric thickening agent containing at least about 3% of cross-linking agent.

7. A composition according to any one of claims 1 to 6 wherein said cross-linked polymeric thickening agent contains a plurality of carboxylic, phosphonic, phosphinic or sulfonic acid or acid salt groups or mixtures thereof.

8. A composition according to claim 7 wherein the said cross-linked polymeric thickening agent is made with a cross-linking agent containing at least two ethylenically unsaturated groups or at least two groups reactive with pendant reactive groups along the polymer chain of the polymeric thickening agent.

9. A composition according to any one of claims 1 to 6 wherein said cross-linking polymeric thickening agent comprises a copolymer of maleic acid or anhydride with another ethylenically unsaturated monomer.

10. A composition according to claim 9 wherein said other monomer comprises methyl vinyl ether.

11. A composition according to claim 10 wherein said copolymer is made with 1,7-octadiene, 1,9-decadiene, or polyethylene glycol as cross-linking agent.

12. A composition according to any one of claims 1 to 6 wherein said cross-linking polymeric thickening agent comprises units of styrene phosphonic acid, vinyl phosphonic acid or mixtures thereof.

13. A method of promoting personal care and hygiene comprising applying to the hair or skin an effective amount of a composition as defined in any one of claims 1 to 6.

14. A method of setting hair comprising applying to the hair an effective amount of a composition as defined in claim 3.

15. A method of promoting skin care and hygiene comprising applying to the skin an effective amount of a composition as defined in any one of claims 4, 5 or 6.

* * * * *